US008288483B2

(12) United States Patent
Ito et al.

(10) Patent No.: US 8,288,483 B2
(45) Date of Patent: Oct. 16, 2012

(54) DIURETHANE COMPOUND, PROCESS FOR PRODUCING THE SAME, AND ACRYLIC RUBBER COMPOSITION CONTAINING THE SAME

(75) Inventors: Daisuke Ito, Kitaibaraki (JP);
Haruyoshi Tatsu, Kitaibaraki (JP);
Keisuke Kokin, Kitaibaraki (JP);
Hideyuki Ono, Kitaibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 57 days.

(21) Appl. No.: 12/919,718

(22) PCT Filed: Jan. 30, 2009

(86) PCT No.: PCT/JP2009/051622
§ 371 (c)(1),
(2), (4) Date: Aug. 26, 2010

(87) PCT Pub. No.: WO2009/096545
PCT Pub. Date: Aug. 6, 2009

(65) Prior Publication Data
US 2011/0040043 A1 Feb. 17, 2011

(30) Foreign Application Priority Data

Jan. 30, 2008 (JP) ................................. 2008-019001

(51) Int. Cl.
*C08C 19/20* (2006.01)
*C08C 19/22* (2006.01)
*C08J 3/24* (2006.01)
*C08F 8/30* (2006.01)

(52) U.S. Cl. ............... 525/330.5; 525/330.4; 525/329.8; 525/329.9; 525/327.3; 525/331.4; 525/347; 525/353; 525/374; 525/375

(58) Field of Classification Search ............... 525/329.8, 525/329.9, 330.4, 330.5, 327.3, 331.4, 347, 525/353, 374, 375
See application file for complete search history.

(56) References Cited

U.S. PATENT DOCUMENTS

| 3,373,156 | A | 3/1968 | Bamberg et al. |
| 4,157,915 | A | 6/1979 | Hamaoka et al. |
| 6,015,860 | A | 1/2000 | Kuzumaki et al. |
| 2008/0200580 | A1* | 8/2008 | Aoki et al. ............... 522/100 |

FOREIGN PATENT DOCUMENTS

| JP | 53-135628 | A | 11/1978 |
| JP | 11-100478 | | 4/1999 |
| JP | 11-140264 | | 5/1999 |
| JP | 11-255997 | A | 9/1999 |
| JP | 2001-181464 | | 7/2001 |
| JP | 2001-512419 | A | 8/2001 |
| JP | 2001-316554 | | 11/2001 |
| JP | 2002-317091 | | 10/2002 |
| JP | 2003-342437 | | 12/2003 |
| JP | 2004-177416 | A | 6/2004 |
| JP | 2004-269873 | A | 9/2004 |
| JP | 2005-017354 | A | 1/2005 |
| JP | 2006-282657 | A | 10/2006 |
| WO | WO 03/004563 | A1 | 1/2003 |
| WO | WO 2005-103143 | A1 | 11/2005 |

OTHER PUBLICATIONS

Arimitsu et al., J. Mater. Chem. 14 (2004) 336-343.*
Arimitsue, et al., *Applications of a nonlinear organic reaction of carbamates to proliferate aliphatic amines*, Angewandte Chemie, International Edition, 2000, vol. 39, No. 19, pp. 3425-3428.
Arimitsue et al., *Nonlinear organic reaction f 9-fluorenylmethyl carbamates as base amplifiers to proliferate aliphatic amines and their application to a novel photopolymer system*; Journal of Materials Chemistry, 2004, vol. 14, No. 3, pp. 336-343.
Arimitsu et al., *Sensitivity enhancement of a photocuring material by base amplifiers*, Journal of Photopolymer Science and Technology, 2000, vol. 13, No. 1, pp. 157-158.
Lu et al., *Liquid chromatography-mass spectrometry studies of 9-fluorenylmethyl chloroformate derivatives of polyamines*, Journal of Chromatography, 1991, vol. 540, pp. 199-206.
Miyamoto et al., *Synthesis of phenylsulfonylethyl carbamates as a base amplifier and their applications to photopolymer systems*, Journal of Photopolymer Science and Technology, 1999, vol. 12, No. 2, pp. 315-316.
International Search Report from corresponding PCT application No. PCT/JP2009/051622 dated Mar. 3, 2009, 4 pages.
International Preliminary Report on Patentability and Written Opinion from corresponding PCT application No. PCT/JP2009/051622 dated Sep. 10, 2010, 9 pages.

* cited by examiner

*Primary Examiner* — Roberto Rabago
(74) *Attorney, Agent, or Firm* — Brinks Hofer Gilson & Lionie

(57) ABSTRACT

Disclosed is a diurethane compound $R^2(SO_2)_m(CH_2)_nO-CONH-R^1-NHCOO(CH_2)_n(SO_2)_mR^2$ produced by a method allowing a diamine compound $H_2NR^1NH_2$ to react with a chloroformate compound $ClCOO(CH_2)_n(SO_2)_mR^2$ or a method allowing a diisocyanate compound $OCNR^1NCO$ to react with a hydroxyl-containing compound $R^2(SO_2)_m(CH_2)_n$ OH. The diurethane compound is compounded with multivalent amine crosslinkable group-containing acrylic rubber together with a basic vulcanization accelerator to form an acrylic rubber composition. The acrylic rubber composition including the diurethane compound as a vulcanizing agent decreases a delay in the vulcanization rate due to prevention of scorching and also allows a vulcanized article to satisfy the compression set characteristics.

12 Claims, No Drawings

DIURETHANE COMPOUND, PROCESS FOR PRODUCING THE SAME, AND ACRYLIC RUBBER COMPOSITION CONTAINING THE SAME

RELATED APPLICATION

This application is a 35 U.S.C. §371 national phase filing of International Patent Application No. PCT/JP2009/051622, filed Jan. 30, 2009, through which and to which priority is claimed under 35 U.S.C. §119 to Japanese Patent Application No. 2008-019001, filed Jan. 30, 2008.

TECHNICAL FIELD

The present invention relates to a novel diurethane compound, a method of producing the same, and an acrylic rubber composition containing the same. More specifically, the present invention relates to a diurethane compound to be used as a novel vulcanizing agent for crosslinkable group-containing acrylic rubber, a method of producing the compound, and an acrylic rubber composition containing the compound.

[Background Art]

Carboxyl group-containing acrylic rubber is particularly excellent in heat resistance and compression set characteristics compared to other acrylic rubber materials and is halogen-free acrylic rubber that is non-corrosive to metals and is environment friendly. Therefore, recently, its use as, for example, hose or seal materials has been increasingly demanded. However, its scorch time is short relative to the vulcanization rate, that is, there is a tendency that the scorch time becomes too short by making the vulcanization rate higher and that the scorch time becomes long by making the vulcanization rate lower.

More specifically, when the vulcanization rate is increased to a satisfactory level, the scorch time becomes short thereby to cause deterioration in a compound flow and poor molding. When the vulcanization rate is decreased, the molding time becomes long thereby to cause an increase in cost. This means poor moldability from the viewpoint of that simultaneously achieving a high vulcanization rate and a long scorch time is ideal.

Vulcanization molding of acrylic rubber is usually performed by molding with mold (e.g., injection molding, compression molding, or transfer molding) or by extrusion molding. Currently, in order to well balance the vulcanization rate and the scorch time during molding, there are flows of the following two vulcanization systems:

(1) aliphatic diamine (vulcanizing agent)/guanidine (vulcanization accelerator), and
(2) aromatic diamine (vulcanizing agent)/guanidine (vulcanization accelerator).

In the aliphatic diamine vulcanization system used in molding with mold mainly preceding the vulcanization rate, the vulcanization rate is higher, but the scorch time is shorter, compared to that in the aromatic diamine vulcanization system used in extrusion molding mainly preceding the scorch time (t5: 10 minutes or more). On the other hand, in the aromatic diamine vulcanization system (using 4,4'-diaminodiphenyl ether, 2,2-bis[4-(4-aminophenoxy)phenyl]propane, methylenedianiline, or the like as the vulcanizing agent), the scorch time is longer than that of the aliphatic diamine vulcanization system, but it has a disadvantage that the vulcanization rate is low. Thus, a vulcanization system achieving both high-rate vulcanization and non-scorch has not been found yet.

Here, with the vulcanization mechanism of the aliphatic diamine vulcanization system considered, hexamethylenediamine carbamate (6-aminohexyl carbamic acid) $H_3N^+(CH_2)_6NHCOO^-$ is widely used as the aliphatic diamine in vulcanization of carboxyl group-containing acrylic rubber or chlorine group-containing acrylic rubber. The vulcanization reaction progresses by applying heat to the vulcanizing agent compound to pyrolytically decarboxylate the protective group of the amino group of hexamethylenediamine at near 100° C. or higher to give hexamethylenediamine, which reacts with a carboxyl group or the like serving as a crosslinkable functional group in the acrylic rubber. Therefore, it has a disadvantage that the scorch time is short (poor in scorch stability). In addition, one of reasons that the hexamethylenediamine is used in a carbonate form is that hexamethylenediamine is high in moisture absorbency and also readily vaporizes and thereby has difficulty in use.

Furthermore, as the carboxyl group-containing acrylic rubber, for example, carboxyl group-containing ethylene acrylic rubber (Vamac G, a product of DuPont) and specific carboxyl group-containing acrylic rubber (Denka ER, a product of Denki Kagaku Kogyo Kabushiki Kaisha) are also included, and such carboxyl group-containing acrylic rubber also has a disadvantage that the scorch time is short.

Incidentally, some of the following Patent Documents include vulcanization systems in which the vulcanization rate is high and, at the same time, the scorch time is long, but some of the systems cannot avoid a decrease in compression set characteristics.

[Patent Document 1] JP-A-11-255997
[Patent Document 2] JP-A-11-100478
[Patent Document 3] JP-A-11-140264
[Patent Document 4] WO 2005/103143
[Patent Document 5] JP-A-2001-181464
[Patent Document 6] JP-A-2001-316554
[Patent Document 7] JP-A-2003-342437
[Patent Document 8] JP-A-2002-317091
[Patent Document 9] JP-A-2004-269873
[Patent Document 10] JP Patent Republication 2003-4563

DISCLOSURE OF THE INVENTION

[Problems to be Solved by the Invention]

It is an object of the present invention to provide a diurethane compound to be used as a novel vulcanizing agent for crosslinkable group-containing acrylic rubber, a method of producing the diurethane compound, and an acrylic rubber composition including the diurethane compound as a vulcanizing agent thereby to decrease a delay in the vulcanization rate due to prevention of scorching, that is, to achieve both a good vulcanization rate of aliphatic diamine and good scorch stability of aromatic diamine and also provide satisfactory physical properties, in particular compression set characteristics, of a vulcanizate.

[Means for Solving the Problems]

The present invention provides a diurethane compound represented by a general formula:

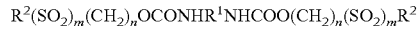

(wherein, $R^1$ is a $C_1$ to $C_{20}$ linear or branched, bivalent aliphatic alkylene group, a bivalent alicyclic cycloalkylene group, or a bivalent aromatic group; $R^2$ is, when it is in a carbamate structure form, a group that is decomposed by the effect of a basic vulcanization accelerator thereby to generate diamine; n is 0, 1, or 2; and m is 0 or 1).

Such a diurethane compound is produced by allowing a diamine compound represented by a general formula $H_2NR^1NH_2$ to react with a chloroformate compound represented by a general formula $ClCOO(CH_2)_n(SO_2)_mR^2$ or allowing a diisocyanate compound represented by a general formula $OCNR^1NCO$ to react with a hydroxyl group-containing compound represented by a general formula $R^2(SO_2)_m(CH_2)_nOH$.

The diurethane compound is compounded with multivalent amine crosslinkable group-containing acrylic rubber together with a basic vulcanization accelerator to form an acrylic rubber composition.

[Effect of the Invention]

The acrylic rubber composition according to the present invention is an acrylic rubber composition compounding a vulcanization system composed of a diurethane compound as a novel compound and a basic vulcanization accelerator and is characterized in that a vulcanization reaction proceeds by the decomposition effect of the basic vulcanization accelerator added to the vulcanization system together with the diurethane compound, unlike that vulcanization reactions of carboxyl group-containing acrylic rubber proceed by thermal decomposition by usual vulcanizing agents. Therefore, when a basic vulcanization accelerator is not simultaneously used, vulcanization does not proceed at all even if a diurethane compound is used as a novel vulcanizing agent.

The diurethane compound to be used as the vulcanizing agent is stable so that it is not thermally decomposed even at 180° C. when it is alone, but is deprotected in the presence of a basic vulcanization accelerator to generate hexamethylenediamine, resulting in promotion of the vulcanization reaction. As a result, for example, injection molding can be performed in a small amount of time, which cannot be realized by conventional diamine vulcanization systems, and also it is possible to vulcanize at a high rate (vulcanization in a small amount of time) and to extrude at a high temperature for extrusion molding, which conventionally cannot use aliphatic diamine vulcanization systems from the standpoint of scorch and therefore has used aromatic diamine vulcanization systems. Extrusion molding needs a scorch time t5 (125° C.) of 10 minutes or more, and this requirement is also satisfied.

Consequently, it is possible to decrease a delay in the vulcanization rate due to prevention of scorching. By thus solving this delay problem that is disadvantageous in, for example, injection molding, the ranges of molding conditions can be broadly set. In addition, decreases in physical properties, in particular in compression set characteristics, of vulcanizate are not observed. As a result, the diurethane compound can be effectively applied to extrusion molding as well as molding by mold such as injection molding, compression molding, and transfer molding and can be effectively used as vulcanization molding material of, for example, various seals, such as oil seals, gaskets, and O rings, hoses, diaphragms, rolls, vibration-isolating rubber, and industrial rubber parts.

BEST MODE FOR CARRYING OUT THE INVENTION

The diurethane compound used as a novel vulcanizing agent and represented by a general formula:

$$R^2(SO_2)_m(CH_2)_nOCONHR^1NHCOO(CH_2)_n(SO_2)_mR^2$$

can be synthesized by the following reactions:
(1) $H_2NR^1NH_2+2ClCOO(CH_2)_n(SO_2)_mR^2$ (chloroformate compound), or
(2) $OCNR^1NCO+2R^2(SO_2)_m(CH_2)_nOH$ (hydroxyl-containing compound).

Here, $R^1$ is a bivalent aliphatic alkylene group having a $C_1$ to $C_{20}$ linear or branched structure, a bivalent alicyclic cycloalkylene group, or a bivalent aromatic group. Examples of the bivalent aliphatic alkylene group include $—(CH_2)_1—$ (1=2 to 20) and $—CH_2C(CH_3)_2CH_2—$; examples of the bivalent alicyclic cycloalkylene group include

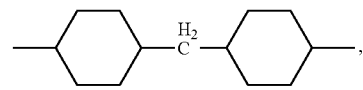

and examples of the bivalent aromatic group include

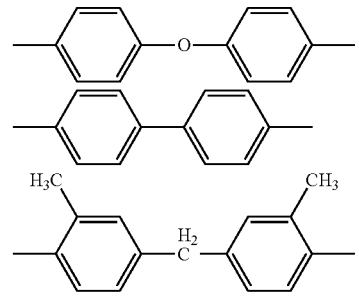

Preferably, a $C_4$ to $C_{10}$ linear alkylene group is used.

$R^2$ is, when it is in a carbamate structure form, a group that is decomposed by the effect of a basic vulcanization accelerator thereby to generate diamine, and is specifically a $C_1$ to $C_{20}$ alkyl, alkoxyl, haloalkyl, olefin, aryl, or aralkyl group, a fluorenyl-containing group, a S-containing group, a Si-containing group, a N-containing group, or a P-containing group. The S-containing group or the N-containing group can be an aromatic or aliphatic heterocyclic group.

Examples of the $R^2$ group include linear or alicyclic alkyl groups such as methyl, ethyl, propyl, isopropyl, diisopropylmethyl, tert-butyl, tert-amyl, cyclobutyl, cyclohexyl, cycloheptyl, and cyclopropylmethyl groups; alkoxyl groups such as methoxy, ethoxy, propoxy, butoxy, phenoxy, and 4-methylphenoxy groups; haloalkyl groups such as 2,2,2-trichloroethyl, 1,1-dimethyl-2-bromoethyl, 1,1-dimethyl-2,2-dibromoethyl, and 1,1-dimethyl-2,2,2-trichloroethyl groups; olefin groups such as vinyl, allyl, 1-isopropylallyl, cinnamyl, and 4-nitrocinnamyl groups; aryl or aralkyl groups such as phenyl, m-nitrophenyl, o-nitrophenyl, 3,4-dimethoxy-6-nitrobenzyl, phenyl(o-nitrophenyl)methyl, benzyl, p-methoxybenzyl, 3,5-dimethoxybenzyl, p-decyloxybenzyl, p-nitrobenzyl, p-bromobenzyl, p-chlorobenzyl, p-cyanobenzyl, 2,4-dichlorobenzyl, m-chloro-p-ethoxybenzyl, 4-methylsulfonylbenzyl, 2-phenylethyl, diphenylethyl, 1-methyl-1-(4-biphenynyl)ethyl, 1-(3,5-di-tert-butylphenyl)-1-methylethyl, and 9-anthrenylmethyl groups; fluorenyl-containing groups such as 9-fluorenylmethyl, 9-(2-sulfo)fluorenylmethyl, and 9-(2,7-dibromo)fluorenylmethyl groups; S-containing groups such as 2-methylthioethyl, 2-methylsulfonylethyl, 2-(p-toluenesulfonyl)ethyl, 4-methylthiophenyl, 2,4-dimethylthiophenyl, [2-(1,3-dithianyl)]methyl, methyldithio, ethyldithio, isopropyldithio, tert-butyldithio, phenyldithio, 2-methylsulfonylethyl, and 2,7-di-tert-butyl[9-(10,10-dioxo-10,10,10,10-tetrahydrothioanyl]methyl; Si-containing groups such as 2-trimethylsilylethyl group; N-containing groups such as 1,1-dimethyl-2-cyanoethyl, 2-(2'-pyridyl) ethyl, 2-(4'-pyridyl)ethyl, dimethyl-2-cyanoethyl, 5-benzoyl oxazoyl, and 2-(N,N-dicyclohexyl carboxamide)ethyl; and P-containing groups such as 2-phosphonioethyl, 2-triphenylphosphonioisopropyl, and 2-(triphenylphosphonio)ethyl groups. Among them, 9-fluorenylmethyl, 9-(2-sulfo)fluorenylmethyl, 9-(2,7-dibromo)fluorenylmethyl, 2-(p-toluenesulfonyl)ethyl, and [2-(1,3-dithianyl)methyl] groups are preferably used, and 9-fluorenylmethyl, 2-(p-toluenesulfonyl)ethyl, and [2-(1,3-dithianyl)methyl] groups are more preferably used.

In the production process (1) of producing the diurethane compound, a mixture of a diamine compound, such as hexamethylenediamine, melted in advance in a hot water bath, 1,4-dioxane, and an aqueous solution of sodium carbonate as a neutralizer is cooled to about 0 to 2° C., and a 1,4-dioxane solution of a chloroformate compound is dropwise added thereto in a molar amount stoichiometrically two or more times based on the amount of the diamine compound at a dropping rate such that the temperature inside the reaction vessel does not rise above 5° C. After completion of the dropping, the resulting mixture is stirred under room temperature conditions for about several hours, followed by addition of water to the reaction mixture. The precipitated solid is collected by filtration to complete the production.

Furthermore, in the production process (2), a hydroxyl group-containing compound and a diisocyanate compound are subjected to a reaction in an organic solvent such as toluene or dioxane at about 75 to 110° C. while stirring and then cooled, followed by collection of the undissolved portion by filtration to complete the production.

The resulting diurethane compound is compounded with multivalent amine crosslinkable group-containing acrylic rubber together with a basic vulcanization accelerator to form an acrylic rubber composition. As the multivalent amine crosslinkable group-containing acrylic rubber, acrylic rubber of which vulcanizing agent is multivalent amine, such as carboxyl group-containing acrylic rubber, epoxy group-containing acrylic rubber, or chlorine group-containing acrylic rubber, is used. Preferably, aliphatic diamine vulcanizing type carboxyl group-containing acrylic rubber is used.

As the carboxyl group-containing acrylic rubber, a copolymer of at least one of alkyl acrylate including an alkyl group having 1 to 8 carbon atoms and alkoxyalkyl acrylate including an alkoxyalkyl group having 2 to 8 carbon atoms and a carboxyl group-containing unsaturated compound is used.

As the alkyl acrylate, for example, methyl acrylate, ethyl acrylate, propyl acrylate, isopropyl acrylate, n-butyl acrylate, n-hexyl acrylate, 2-ethyl hexyl acrylate, n-octyl acrylate, or methacrylate corresponding to such acrylate is used. In general, an alkyl group having a longer chain is advantageous from the standpoint of cold resistance, but is disadvantageous in oil resistance. In a shorter chain, an inverse tendency is observed. Therefore, ethyl acrylate and n-butyl acrylate are preferably used from well balanced oil resistance and cold resistance.

In addition, as the alkoxyalkyl acrylate, for example, methoxymethyl acrylate, methoxyethyl acrylate, ethoxyethyl acrylate, n-butoxyethyl acrylate, or ethoxypropyl acrylate is used. Preferably, 2-methoxyethyl acrylate or 2-ethoxyethyl acrylate is used. The alkoxyalkyl acrylate and the alkyl acrylate may be respectively used alone, but are preferably used in a ratio of 60 to 0 wt % of the former and 40 to 100 wt % of the latter. Copolymerization of the alkoxyalkyl acrylate achieves a favorable balance between oil resistance and cold resistance, but a ratio of the copolymerized alkoxyalkyl acrylate higher than the above has a tendency that the normal state physical properties and heat resistance are decreased.

Examples of the carboxyl group-containing unsaturated compound include monoalkyl esters of maleic acid or fumaric acid, such as methyl, ethyl, propyl, isopropyl, n-butyl, and isobutyl esters; and monoalkyl esters of itaconic acid or citraconic acid, such as methyl, ethyl, propyl, isopropyl, n-butyl, and isobutyl esters; and maleic acid mono-n-butyl ester, fumaric acid monoethyl ester, and fumaric acid mono-n-butyl ester are preferably used. In addition to them, unsaturated monocarboxylic acid such as acrylic acid or methacrylic acid is used. These carboxyl group-containing unsaturated compounds are used at a copolymerization ratio of about 0.5 to 10 wt %, preferably about 1 to 7 wt %, in a carboxyl group-containing acrylic elastomer. When the copolymerization ratio is lower than the above, the vulcanization is insufficient thereby to deteriorate the value of compression set. On the other hand, a copolymerization ratio higher than the above readily causes scorching. Incidentally, since the copolymerization reaction is performed in such a manner that the polymerization conversion rate is 90% or more, the weight ratio of each charged monomer is approximately the copolymer component weight ratio of the resulting copolymer.

In the carboxyl group-containing acrylic elastomer, another copolymerizable ethylenic unsaturated monomer, such as styrene, α-methylstyrene, vinyltoluene, vinylnaphthalene, (meth)acrylonitrile, acrylic acid amide, vinyl acetate, cyclohexyl acrylate, benzyl acrylate, 2-hydroxyethyl acrylate, 4-hydroxybutyl acrylate, ethylene, propylene, piperylene, butadiene, isoprene, or pentadiene, can be further copolymerized at a ratio of about 50 wt % or less.

Furthermore, according to need, in order to improve kneading processability, extrusion processability, or the like, a multi-functional (meth)acrylate or oligomer having a glycol residue at the side chain, for example, di(meth)acrylate of alkylene glycol, such as ethylene glycol, propylene glycol, 1,4-butandiol, 1,6-hexanediol, or 1,9-nonanediol; di(meth)acrylate of, e.g. neopentylglycol, tetraethyleneglycol, tripropyleneglycol, or polypropyleneglycol; bisphenol A ethylene oxide adduct diacrylate; dimethylol tricyclodecane diacrylate, glycerine methacrylate acrylate, or 3-acryloyloxy glycerine monomethacrylate, can be used for further copolymerization.

As the epoxy group-containing rubber, an epoxy group-containing unsaturated compound, such as vinyl glycidyl ether, allyl glycidyl ether, glycidyl acrylate, or glycidyl methacrylate, is used for copolymerization, instead of the carboxyl group-containing unsaturated compound in carboxyl group-containing acrylic rubber, at a copolymerization ratio of about 0.5 to 10 wt %, preferably about 1 to 5 wt %, in an epoxy group-containing acrylic elastomer.

Furthermore, as the chlorine group-containing acrylic rubber, a chlorine group-containing unsaturated compound, such as chloroethyl vinyl ether, chloroethyl acrylate, vinyl benzyl chloride, vinyl chloroacetate, or allyl chloroacetate, is used for copolymerization, instead of the carboxyl group-containing unsaturated compound in carboxyl group-containing acrylic rubber, at a copolymerization ratio of about 0.1 to 15 wt %, preferably about 0.3 to 5 wt %, in chlorine group-containing acrylic rubber. In particular, active chlorine group-containing acrylic rubber is formed by copolymerizing vinyl chloroacetate or the like as the chlorine group-containing unsaturated compound.

The diurethane compound serving as a vulcanizing agent is used at a ratio of about 0.1 to 10 parts by weight, preferably about 0.5 to 5 parts by weight, based on 100 parts by weight of the multivalent amine crosslinkable group-containing acrylic elastomer. When the vulcanizing agent is used at a ratio less than above, the vulcanization is insufficient, resulting in insufficient physical properties such as tensile strength, compression set, and so on. On the other hand, a ratio higher than the above causes a decrease in elongation at break and a deterioration in compression set.

The diurethane compound vulcanizing agent is used together with a basic vulcanization accelerator. As the basic vulcanization accelerator, for example, a guanidine compound, 1,8-diazabicyclo[5.4.0]undecene-7, or 1,5-diazabicyclo[4.3.0]nonene-5 is used. In addition, a mixture of 1,8-diazabicyclo[5.4.0]undecene-7 and silica can be used. Actually, for example, Vulcofac ACT55, a product of Safic Alcan, is used.

As the guanidine, guanidine or its substituent, such as aminoguanidine, 1,1,3,3-tetramethylguanidine, n-dodecylguanidine, methylolguanidine, dimethylolguanidine, 1-phenylguanidine, 1,3-diphenylguanidine, 1,3-di-o-tolyl guanidine, triphenylguanidine, 1-benzyl-2,3-dimethylguanidine, or cyanoguanidine, is used. In addition, for example, 1,6-guanidinohexane, guanylurea, biguanide, and 1-o-tolyl biguanide can be used.

Based on 100 parts by weight of the multivalent amine crosslinkable group-containing acrylic rubber, the guanidine serving as a basic vulcanization accelerator is used at a ratio of about 0.1 to 10 parts by weight, preferably about 0.3 to 6 parts by weight, and the diaza compound is used at a ratio of about 0.01 to 1 parts by weight, preferably about 0.03 to 0.5 parts by weight. The mixture of 1,8-diazabicyclo[5.4.0]undecene-7 and silica is used at a ratio of about 0.1 to 10 parts by weight, preferably about 0.2 to 5 parts by weight, based on 100 parts by weight of the multivalent amine crosslinkable group-containing acrylic rubber. When the addition ratio of the basic vulcanization accelerator is less than the above, vulcanization does not progress even if the diurethane compound vulcanizing agent is used. On the other hand, a ratio higher than the above makes scorching short, which is undesirable.

The vulcanization reaction using such a novel vulcanization system will be reviewed. The diurethane compound of the present invention is not decomposed at 100° C., which is a temperature at which conventionally used hexamethylenediamine carbamate is deprotected, but is decomposed by the effect of a basic vulcanization accelerator.

More specifically, when an alkylene diamine compound, preferably $H_2N(CH_2)_nNH_2$ (n=4 to 6), particularly preferably hexamethylenediamine (in the formula, n=6) is subjected to a reaction with 9-fluorenylmethyl chloroformate, to give a derivative in which the amino group of the hexamethylenediamine is protected with a 9-fluorenylmethyl oxycarbonyl group [Fmoc], and the resulting derivative is used alone as a vulcanizing agent [HMDA-Fmoc], vulcanization does not proceed at the decarbonation temperature of hexamethylenediamine carbamate, but proceeds by the effect of a basic vulcanization accelerator to generate hexamethylenediamine. Therefore, vulcanization at a high rate and high scorch resistance can be realized while maintaining desired physical properties of vulcanizate by suitably controlling the compounding amount of the basic vulcanization accelerator.

It is anticipated that the reaction mechanism is expressed by the following expression:

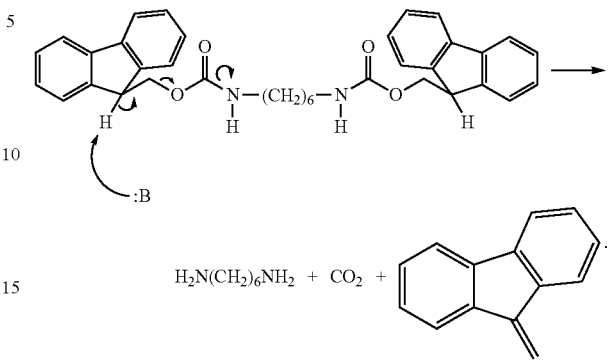

Furthermore, it is anticipated that the reaction mechanism of a diurethane compound disubstituted by a [2-(1,3-dithianyl)methyl] group [HMDA-Dmoc] is expressed by the following expression:

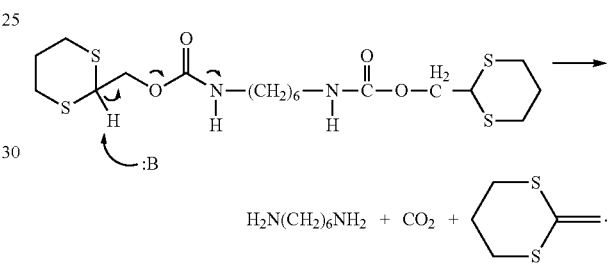

The acrylic rubber composition is prepared by kneading the carboxyl group-containing acrylic rubber and rubber compounding ingredients that are usually used, for example, an inorganic filler such as carbon black or silica, a lubricant, an antioxidant, and other necessary compounding ingredients, with a sealed kneader such as a Banbury mixer, then adding a vulcanizing agent and a vulcanization accelerator thereto, and mixing them using an open roll. The prepared acrylic rubber composition is usually press-vulcanized at about 150 to 200° C. for about 1 to 60 minutes and, according to need, oven-vulcanized at about 150 to 200° C. for about 1 to 10 hours.

EXAMPLES

The present invention will now be described with reference to examples.

Example 1

Into a 500-mL four-neck flask equipped with a thermometer, a dropping funnel, and a stirrer, 5.42 g (46.6 mmol) of hexamethylenediamine (a product of Wako Pure Chemical Industries) melted in advance in a hot water bath at 50° C., 160 mL of 1,4-dioxane (a product of Tokyo Chemical Industry), and 124 mL of an aqueous solution of 10 wt % sodium carbonate (a product of Wako Pure Chemical Industries) were charged in this order and then cooled to 0° C.

A solution prepared by dissolving 24.8 g (93.2 mmol) of 9-fluorenylmethyl chloroformate (a product of Aldrich):

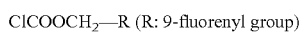

ClCOOCH$_2$—R (R: 9-fluorenyl group)

in 120 mL of 1,4-dioxane was dropped through the dropping funnel at a dropping rate such that the temperature inside the reaction vessel did not rise above 5° C. After completion of the dropping, the resulting mixture was stirred under room temperature conditions for 6 hours. After completion of the reaction, 200 mL of water was added to the reaction mixture, and the precipitated solid was collected by filtration.

The precipitated solid was dried at 45° C. for 12 hours under reduced pressure to obtain 25.3 g (yield: 96.7%) of a white powdery solid [HMDA-Fmoc]:

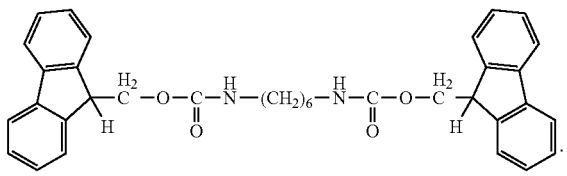

The structure of the obtained solid was identified by $^1$H NMR and FT-IR.

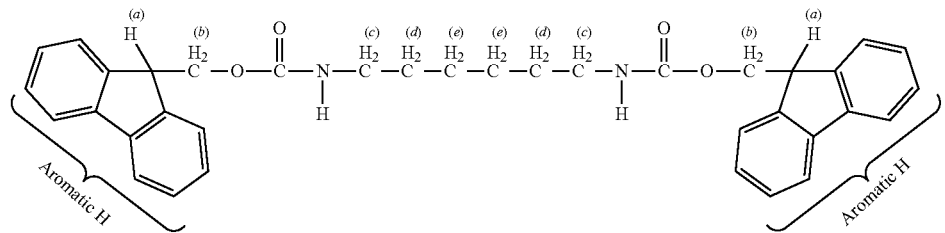

$^1$H NMR:
(a) 4.2 ppm (t 2H)
(b) 4.4 ppm (d 4H)
(c) 3.2 ppm (q 4H)
(d) 1.5 ppm (m 4H)
(e) 1.3 ppm (m 4H)
Aromatic H, 7.2-7.8 ppm (m 16H)
FT-IR: 3335 cm$^{-1}$: N—H stretching vibration of secondary amine
1686 cm$^{-1}$: C=O stretching vibration originated urethane bond Example 2

Into a 200-mL three-neck flask equipped with a thermometer, a reflux cooling tube, and a stirrer, 11.91 g (59.7 mmol) of 2-(p-toluenesulfonyl)ethanol HOCH$_2$CH$_2$SO$_2$(p-C$_6$H$_4$)CH$_3$, 5.00 g (29.4 mmol) of hexamethylene diisocyanate, and 100 mL of toluene were charged. The reaction vessel was heated to 80° C., and the mixture was stirred for 8 hours.

After completion of the reaction, the mixture was cooled. The undissolved portion was collected by filtration and dried at 45° C. for 12 hours under reduced pressure to obtain 14.6 g (yield: 86.5%) of a white powdery solid [HMDA-Tsec]:

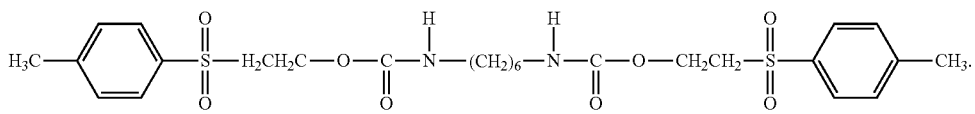

The structure of the obtained solid was identified by $^1$H NMR and FT-IR.

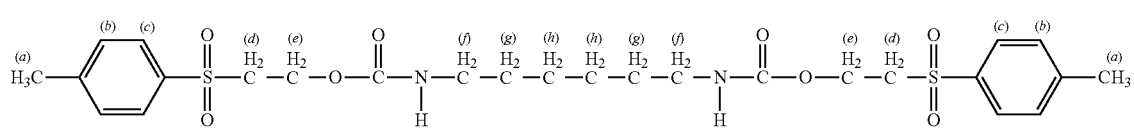

¹H NMR:
(a) 2.45 ppm (s 6H)
(b), (c) 7.2-7.8 ppm (m 8H)

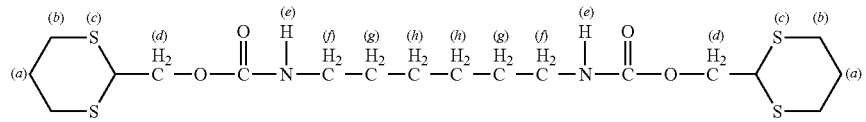

(d) 3.4 ppm (t 4H)
(e) 4.4 ppm (t 4H)
(f) 3.1 ppm (q 4H)
(g) 1.6 ppm (m 4H)
(h) 1.3 ppm (m 4H)
FT-IR: 3339 cm$^{-1}$: N—H stretching vibration of secondary amine
1693 cm$^{-1}$: C=O stretching vibration originated urethane bond
1322, 1142 cm$^{-1}$: sulfone bond (—SO$_2$—)

Example 3

(1) Into a 5-L round-bottom flask, 2 L of tert-butyl methyl ether and 253.3 g (1.2 mol) of a 2-(ethoxycarbonyl)-1,3-dithiane crude product synthesized by a known method were charged, and 148.2 g (3.9 mol) of NaBH$_4$ was further charged. The round-bottom flask was equipped with a dropping funnel, and 650 mL of methanol was charged in the funnel and was dropped over 3 hours or more under room temperature conditions. After completion of the dropping, the mixture was stirred at 40 to 45° C. for 5 hours.

After completion of the reaction, the mixture was cooled to room temperature and was then concentrated to approximately a half-volume, followed by addition of 1N hydrochloric acid. The resulting mixture was extracted with 800 mL of ethyl acetate three times, and the organic layer was washed with brine and was dried over magnesium sulfate, followed by distillation under reduced pressure. The undissolved portion was collected by filtration to obtain 142 g (yield: 78.8%) of the target precursor 1,3-dithionyl-2-methanol.

¹H NMR:

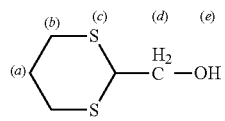

(a) 2.0 ppm (m 21H)
(b) 2.8 ppm (m 4H)
(c) 3.9 ppm (t 11H)
(d) 3.8 ppm (d 2H)
(e) 3.0 ppm (br 1H)

(2) Into a 5-L round-bottom flask equipped with a reflux cooling tube, 67.4 g of triethylamine, 100 g (0.67 mol) of 1,3-dithionyl-2-methanol, 53.3 g (0.35 mol) of 1,6-diisocyanate hexane, and 1.8 L of 1,4-dioxane were charged and refluxed at 100° C. for 4 hours. After completion of the reaction, the reaction mixture was concentrated to about 200 mL, followed by addition of 800 mL of ethanol. The resulting mixture was further refluxed. The reaction mixture was cooled to room temperature, and the precipitated solid was collected by filtration, followed by purification by flash chromatography and recrystallization from ethanol to obtain 107 g (yield: 65%) of the target compound [HMDA-Dmoc].

¹H NMR:

(a) 2.0 ppm (m 4H)
(b) 2.8 ppm (m 8H)
(c) 4.1 ppm (t 2H)
(d) 4.4 ppm (d 4H)
(e) 4.9 ppm (br 2H)
(f) 3.2 ppm (m 4H)
(g) 1.5 ppm (m 41-1)
(h) 1.3 ppm (m 4H)

Example 4

| | |
|---|---|
| Aliphatic diamine vulcanizing type carboxyl group-containing acrylic rubber (Noxtite PA-522HF, a product of Unimatec) | 100 parts by weight |
| FEF carbon black (N550) | 60 parts by weight |
| Stearic acid | 1 part by weight |
| 4,4'-(α,α-dimethylbenzyl)diphenylamine (Nocrac CD, a product of Ouchi Shinko Chemical) | 2 parts by weight |
| HMDA-Fmoc | 1.5 parts by weight |
| 1,3-di-o-tolyl guanidine (Nocceler DT, a product of Ouchi Shinko Chemical) | 0.5 parts by weight |

The above-mentioned components excluding the vulcanizing agent and the vulcanization accelerator were kneaded with a Banbury mixer, and then the vulcanizing agent and the vulcanization accelerator were added thereto using an open roll. The thus prepared acrylic rubber composition was press-vulcanized at 180° C. for 8 minutes and oven-vulcanized at 175° C. for 4 hours.

The vulcanizing characteristics and vulcanizate physical properties of the acrylic rubber composition, that is compound, were measured as follows:

Mooney scorch test: according to JIS K6300-1 (125° C.)
  In MLmin, the longer the value (unit: min) of t5, the lower the concern for compound scorching in molding and thereby smaller the defects caused by scorching
  In general, when the value of t5 is 10 minutes or more, defects caused by scorching in injection molding, compression molding, or extrusion molding are small
Vulcanization test: according to JIS K6300-2 (180° C. for 12 minutes)
  A rotorless rheometer RLR-3, a product of Toyo Seiki Seisaku-sho, was used
  The vulcanization rate can be evaluated by tc10, tc90, and ME (MH-ML) of a vulcanization test, and the shorter the tc10 and the tc90 and the larger the ME, the higher the vulcanization rate
Normal state value: according to JIS K6251 and JIS K 6253
Compression set: according to JIS K6262 (150° C. or 175° C. for 70 hours)

Example 5

In Example 4, the amount of 1,3-di-o-tolyl guanidine was changed to 1 part by weight.

Example 6

In Example 4, the amount of 1,3-di-o-tolyl guanidine was changed to 2 parts by weight.

Example 7

In Example 6, 1.75 parts by weight of HMDA-Tsec was used instead of HMDA-Fmoc.

Example 8

In Example 7, the amount of 1,3-di-o-tolyl guanidine was changed to 4 parts by weight.

Example 9

In Example 4, 1 part by weight of a mixture (Vulcofac ACT55, a product of Safic Alcan) of 1,8-diazabicyclo[5.4.0]undecene-7 and silica was used instead of 1,3-di-o-tolyl guanidine.

Example 10

In Example 4, 0.2 parts by weight of 1,8-diazabicyclo[5.4.0]undecene-7 was used instead of 1,3-di-o-tolyl guanidine.

Example 11

In Example 4 the following components were used.

| | |
|---|---|
| Carboxyl group-containing ethylene acrylic rubber (Vamac G, a product of DuPont) | 100 parts by weight |
| FEF carbon black (N550) | 50 parts by weight |
| Stearic acid | 1 part by weight |
| 4,4'-($\alpha$,$\alpha$-dimethylbenzyl)diphenylamine (Nocrac CD) | 2 parts by weight |
| HMDA-Fmoc | 3.75 parts by weight |
| 1,3-di-o-tolyl guanidine (Nocceler DT) | 4 parts by weight |

Example 12

In Example 4, the following components were used.

| | |
|---|---|
| Epoxy group-containing acrylic rubber (Noxtite PA-312, a product of Unimatec) | 100 parts by weight |
| FEF carbon black (N550) | 60 parts by weight |
| Stearic acid | 1 part by weight |
| 4,4'-($\alpha$,$\alpha$-dimethylbenzyl)diphenylamine (Nocrac CD) | 2 parts by weight |
| HMDA-Fmoc | 1.75 parts by weight |
| 1,3-di-o-tolyl guanidine (Nocceler DT) | 2 parts by weight |

Example 13

In Example 12, the same amount of active chlorine group-containing acrylic rubber (Noxtite PA-402K, a product of Unimatec) was used instead of epoxy group-containing acrylic rubber.

Example 14

In Example 12, the same amount of chlorine group-containing acrylic rubber (Noxtite PA-212, a product of Unimatec) was used instead of epoxy group-containing acrylic rubber, and the amount of HMDA-Fmoc was changed to 2.25 parts by weight.

Comparative Example 1

In Example 6, 0.5 parts by weight of hexamethylenediamine carbamate (Cheminox AC-6, a product of Unimatec) was used instead of HMDA-Fmoc.

Comparative Example 2

In Example 6, 0.5 parts by weight of 4,4-diaminodiphenyl ether was used instead of HMDA-Fmoc.

Comparative Example 3

In Comparative Example 1, 1,3-di-o-tolyl guanidine was not used.

Comparative Example 4

In Example 4, 1,3-di-o-tolyl guanidine was not used.

Comparative Example 5

In Example 7, 1,3-di-o-tolyl guanidine was not used.

Comparative Example 6

In Example 9, 0.5 parts by weight of hexamethylenediamine carbamate (Cheminox AC-6) was used instead of HMDA-Fmoc.

Comparative Example 7

In Example 10, 0.5 parts by weight of hexamethylenediamine carbamate (Cheminox AC-6) was used instead of HMDA-Fmoc.

Comparative Example 8

In Example 11, 1.25 parts by weight of hexamethylenediamine carbamate (Cheminox AC-6) was used instead of HMDA-Fmoc.

The results obtained in Examples and Comparative Examples above are shown in the following Table 1 (Examples) and Table 2 (Comparative Examples).

TABLE 1

| | (Examples) | | | | | | | | | | |
|---|---|---|---|---|---|---|---|---|---|---|---|
| Measurement | Example | | | | | | | | | | |
| Item | 4 | 5 | 6 | 7 | 8 | 9 | 10 | 11 | 12 | 13 | 14 |
| Mooney scorch test | | | | | | | | | | | |
| $ML_{min}$ (pts) | 36 | 37 | 38 | 36 | 35 | 36 | 38 | 25 | 42 | 42 | 42 |
| t5 (min) | >60 | 30.5 | 11.3 | >60 | 25.4 | >60 | >60 | 19.4 | 10.8 | 24.7 | 33.4 |
| Vulcanization test | | | | | | | | | | | |
| tc10 (min) | 2.74 | 1.40 | 0.68 | 1.78 | 1.68 | 1.23 | 1.58 | 1.22 | 1.08 | 2.75 | 3.18 |
| tc90 (min) | 9.20 | 7.75 | 3.88 | 9.18 | 8.56 | 6.81 | 8.15 | 4.34 | 8.40 | 8.67 | 9.39 |
| ML (N · m) | 0.16 | 0.15 | 0.16 | 0.15 | 0.14 | 0.16 | 0.17 | 0.05 | 0.17 | 0.19 | 0.19 |
| MH (N · m) | 0.41 | 0.72 | 0.76 | 0.29 | 0.59 | 0.76 | 0.72 | 0.97 | 0.55 | 0.90 | 0.65 |
| ME (MH − ML) (N · m) | 0.25 | 0.57 | 0.6 | 0.14 | 0.45 | 0.6 | 0.55 | 0.92 | 0.38 | 0.71 | 0.46 |
| Normal state value | | | | | | | | | | | |
| Hardness (Duro-A) | 65 | 66 | 65 | 62 | 66 | 66 | 64 | 70 | 70 | 66 | 69 |
| 100% tensile stress (MPa) | 2.5 | 3.5 | 3.4 | 2.4 | 3.5 | 3.4 | 2.9 | 4.1 | 6.9 | 5.1 | 5.8 |
| Tensile strength (MPa) | 9.2 | 9.4 | 9.6 | 8.4 | 9.2 | 10.3 | 9.9 | 16.5 | 12.3 | 11.9 | 10.6 |
| Elongation at break (%) | 310 | 280 | 290 | 380 | 310 | 270 | 290 | 430 | 180 | 200 | 190 |
| Compression set | | | | | | | | | | | |
| 150° C., 70 h (%) | 9 | 8 | 8 | 21 | 12 | 10 | 14 | 13 | 36 | 17 | 32 |
| 175° C., 70 h (%) | 15 | 11 | 10 | 29 | 20 | 18 | 18 | 16 | 55 | 24 | 46 |

TABLE 2

| | (Comparative Examples) | | | | | | | |
|---|---|---|---|---|---|---|---|---|
| Measurement | Comparative Example | | | | | | | |
| Item | 1 | 2 | 3 | 4 | 5 | 6 | 7 | 8 |
| Mooney scorch test | | | | | | | | |
| $ML_{min}$ (pts) | 42 | 38 | 43 | 43 | 42 | 46 | 45 | 31 |
| t5 (min) | 4.8 | 8.7 | 5.2 | >60 | >60 | 3.6 | 4 | 6.1 |
| Vulcanization test | | | | | | | | |
| tc10 (min) | 0.51 | 1.29 | 0.67 | 1.14 | 1.31 | 0.45 | 0.52 | 0.82 |
| tc90 (min) | 3.69 | 8.19 | 6.76 | 9.05 | 9.43 | 4.44 | 5.39 | 4.55 |
| ML (N · m) | 0.17 | 0.16 | 0.18 | 0.15 | 0.15 | 0.18 | 0.18 | 0.06 |
| MH (N · m) | 0.81 | 0.66 | 0.54 | 0.15 | 0.15 | 0.82 | 0.75 | 1.12 |
| ME (MH − ML) (N · m) | 0.64 | 0.5 | 0.36 | 0 | 0 | 0.64 | 0.57 | 1.06 |
| Normal state value | | | | | | | | |
| Hardness (Duro-A) | 64 | 68 | 61 | not molded | not molded | 65 | 64 | 70 |
| 100% tensile stress (MPa) | 3.8 | 4.2 | 2.4 | not molded | not molded | 4 | 3.7 | 4.8 |
| Tensile strength (MPa) | 10.4 | 11.1 | 9.2 | | | 11 | 10.5 | 17.5 |
| Elongation at break (%) | 240 | 270 | 320 | | | 210 | 210 | 340 |
| Compression set | | | | | | | | |
| 150° C., 70 h (%) | 8 | 11 | 22 | | | 12 | 15 | 13 |
| 175° C., 70 h (%) | 12 | 15 | 37 | | | 19 | 20 | 19 |

Example 15

| | |
|---|---|
| Aliphatic diamine vulcanizable type carboxyl group-containing acrylic rubber (Noxtite PA-522HF) | 100 parts by weight |
| FEF carbon black (N550) | 60 parts by weight |
| Stearic acid | 1 part by weight |
| 4,4'-($\alpha,\alpha$-dimethylbenzyl)diphenylamine (Nocrac CD) | 2 parts by weight |
| HMDA-Dmoc | 1.5 parts by weight |
| 1,3-di-o-tolyl guanidine (Nocceler DT) | 2 parts by weight |

By using the components shown above, an acrylic rubber composition was prepared and vulcanized as in Example 4.

The vulcanizing characteristics and vulcanizate physical properties of the acrylic rubber composition, that is compound, were measured as in Example 4.

Example 16

In Example 15, the amount of 1,3-di-o-tolyl guanidine was changed to 4 parts by weight.

Comparative Example 9

In Example 15, 1,3-di-o-tolyl guanidine was not used.

The results obtained in Examples 15 and 16 and Comparative Example 9 are shown in the following Table 3.

TABLE 3

| Measurement Item | | Example 15 | Example 16 | Comparative Example 9 |
|---|---|---|---|---|
| Mooney scorch test | | | | |
| $ML_{min}$ | (pts) | 36 | 36 | |
| t5 | (min) | >60 | 22.3 | >60 |
| Vulcanization test | | | | |
| tc10 | (min) | 1.65 | 1.61 | |
| tc90 | (min) | 8.92 | 8.10 | |
| ML | (N·m) | 0.15 | 0.16 | |
| MH | (N·m) | 0.32 | 0.69 | |
| ME (MH − ML) | (N·m) | 0.17 | 0.53 | |
| Normal state value | | | | |
| Hardness | (Duro-A) | 62 | 64 | Not molded |
| 100% tensile stress | (MPa) | 2.8 | 3.6 | |
| Tensile strength | (MPa) | 8.9 | 9.2 | |
| Elongation at break | (%) | 340 | 280 | |
| Compression set | | | | |
| 150° C., 70 h | (%) | 18 | 14 | |
| 175° C., 70 h | (%) | 26 | 20 | |

The results of Table 3 show the followings:

(1) In Comparative Example 9 in which the measurement with the rheometer was conducted at 180° C., the vulcanization torque was not increased, and the vulcanization did not proceed. This shows that the product obtained in Example 3 (2) is not thermally decomposed at 180° C.

(2) In addition, Examples 15 and 16 prove that the biscarbamate structure is decomposed in the presence of a basic compound such as 1,3-di-o-tolyl guanidine to generate hexamethylenediamine.

The invention claimed is:

1. An acrylic rubber composition comprising a diurethane compound represented by a general formula:

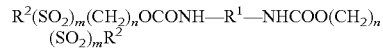

(wherein $R^1$ is a $C_1$ to $C_{20}$ linear or branched, bivalent aliphatic alkylene group, a bivalent alicyclic cycloalkylene group, or a bivalent aromatic group; $R^2$ is a fluorenyl- containing group, n is 0, 1, or 2, and m is 0 or 1), serving as a vulcanizing agent in a ratio of 0.1 to 10 parts by weight and 1,8-diazabicyclo[5.4.0]undecene-7, serving as a basic vulcanization accelerator in a ratio of 0.01 to 1 parts by weight, based on 100 parts by weight of the multivalent amine crosslinkable group-containing acrylic rubber.

2. The acrylic rubber composition according to claim 1, wherein the diurethane compound is represented by the formula:

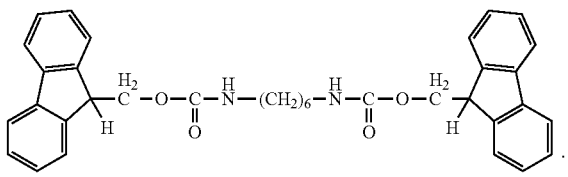

3. The acrylic rubber composition according to claim 1, wherein the multivalent amine crosslinkable group-containing acrylic rubber is a carboxyl group-containing acrylic rubber, an epoxy group-containing acrylic rubber, or a chlorine group-containing acrylic rubber.

4. The acrylic rubber composition according to claim 1, wherein 1,8-diazabicyclo[5.4.0]undecene-7 as the basic vulcanization accelerator is used as a mixture of silica, in a ratio of 0.1 to 10 parts by weight are used based on 100 parts by weight of the multivalent amine crosslinkable group-containing acrylic rubber.

5. A vulcanized molded article molded by mold from an acrylic rubber composition according to claim 1.

6. A vulcanized molded article extrusion-molded from an acrylic rubber composition according to claim 1.

7. A vulcanized molded article molded by mold from an acrylic rubber composition according to claim 2.

8. A vulcanized molded article extrusion-molded from an acrylic rubber composition according to claim 3.

9. A vulcanized molded article molded by mold from an acrylic rubber composition according to claim 4.

10. A vulcanized molded article molded by mold from an acrylic rubber composition according to claim 2.

11. A vulcanized molded article molded by mold from an acrylic rubber composition according to claim 3.

12. A vulcanized molded article extrusion-molded from an acrylic rubber composition according to claim 4.

* * * * *